United States Patent
Fox et al.

(12)

(10) Patent No.: US 6,313,320 B1
(45) Date of Patent: Nov. 6, 2001

(54) PROCESS FOR THE PREPARATION OF CALANOLIDE PRECURSORS

(75) Inventors: Martin Edward Fox; Graham Andrew Meek, both of Cambridge (GB)

(73) Assignee: Chirotech Technology, Inc. (GB)

( * ) Notice: Subject to any disclaimer, the term of this patent is extended or adjusted under 35 U.S.C. 154(b) by 0 days.

(21) Appl. No.: 09/557,544

(22) Filed: Apr. 25, 2000

(30) Foreign Application Priority Data

Apr. 26, 1999 (GB) .................................................. 9909592

(51) Int. Cl.⁷ ................................................ C07D 493/00
(52) U.S. Cl. .............................................................. 549/282
(58) Field of Search .............................................. 549/282

(56) References Cited

U.S. PATENT DOCUMENTS 5,840,921  11/1998  Flavin et al. ........................ 549/282

FOREIGN PATENT DOCUMENTS 9414789  7/1994  (WO) .

OTHER PUBLICATIONS

Desai, R. D. et al. (1957) "Heterocyclic compounds. XXXI. Synthesis of partially methylated esters of polyhydroxy coumarins" *Chemical Abstracts*, vol. 51, No. 19, Oct. 10, 1957, Columbus, Ohio, U.S.; abstract No. XP–00212876.

Games, D. E. et al. (1971) "Synthesis of Some Dimethylpyrano–and 3–Methylbut–2–enyl–4–phenyl–and –4–n–propyl–coumarins" *Chemical Communications* pp. 1005–1006.

Trost, B. M. et al. (1998) "A Catalytic Enantioselective Approach to Chromans and Chromanols. A Total Synthesis of (—)–Calanolides A and B and the Vitamin E Nucleus" *J. Am. Chem. Soc.* 120:9074–9075.

Deshpande, P. P. et al. (1995) "Synthesis of Optically Active Calanolides A and B" *J. Org. Chem.* 60:2964–2965.

*Primary Examiner*—Amelia Owens
(74) *Attorney, Agent, or Firm*—Saliwanchik, Lloyd & Saliwanchik

(57) ABSTRACT

The present invention concerns compounds of the formula

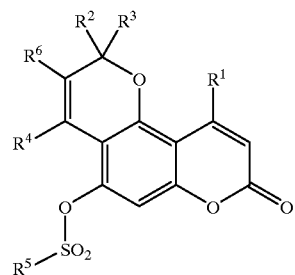

wherein $R^1$, $R^2$, $R^3$, $R^4$ and $R^6$ each represent H or an organic group of up to 20 C atoms, or any pair of $R^2$ and $R^3$ or $R^2$ and $R^6$ or $R^4$ and $R^6$ forms a cyclic group, and $R^5SO_2$ is a cleavable protecting group in which $R^5$ is an organic group of up to 20 C atoms. These compounds are useful as intermediates in the synthesis of calanolide A and related antiviral compounds.

18 Claims, No Drawings

PROCESS FOR THE PREPARATION OF CALANOLIDE PRECURSORS

FIELD OF THE INVENTION

This invention relates to the preparation of a class of tricyclic monophenols which are key intermediates in the synthesis of the calanolide group of xanthones.

BACKGROUND OF THE INVENTION

A family of xanthone natural products with antiviral activity has been isolated from plants of the genus Calophyllum. In particular, (+)-calanolide A, isolated from *Calophyllum lanigerum* var *austroconiaceum* is a potent inhibitor of HIV-1 reverse transcriptase (Galinis et al, *J. Med Chem.*, 1996, 39, 4507 and references contained therein). The structures of certain such;compounds are as follows.

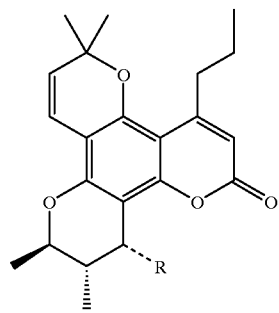

R = ▬OH Calanolide A
R = ⋯OH Calanolide B
ent-Calanolide B = Costatolide

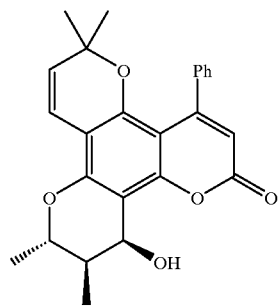

Soulattrolide

A number of syntheses of calanolide A have been reported. See, for example, Chenera et al, *J. Org. Chem.*, 1993, 58, 5605; Deshpande et al, *J. Org. Chem.*, 1995, 60, 2964; Rehder and Kepler, *Synth. Commun.*, 1996 26 4005; Khilevich et al, *Tetrahedron: Asymmetry*, 1996, 7, 3315; Flavin et al, *J. Med Chem.*, 1996, 39, 1303; and Trost and Toste, *J. Am. Chem. Soc.*, 1998, 120, 9074.

Of the reported syntheses of calanolide A, only the syntheses of Deshpande et al and Trost and Toste are asymmetric. In particular, only the synthesis of Trost and Toste uses asymmetric catalysis in the key stereodifferentiating reaction, which comprises palladium-catalysed asymmetric allylic substitution of tiglyl methyl carbonate with 5-hydroxy-2,2-dimethyl-10-propyl-2H-pyrano[2,3-f]chroman-8-one. Following asymmetric allylic substitution, benzylic oxidation with DDQ is used to introduce the unsaturation in the C ring, and further steps to calanolide B comprise diastereoselective hydroboration, Dess Martin oxidation, and cyclisation with zinc chloride. Calanolide A is obtained by Mitsunobu inversion of calanolide B. This methodology is readily extended to the preparation of natural and unnatural analogues of calanolides A and B.

An alternative nucleophile in the asymmetric allylic substitution reaction of Trost and Toste or other D-ring annulation procedures, which would result in a shorter overall synthesis by elimination of the C-ring dehydrogenation step, would be 5-hydroxy-2,2-dimethyl-10-propyl-2H-pyrano[2,3-f]chromen-8-one (in which the C-ring double bond is already present). This compound was originally prepared by unselective 1-step chromene annulation of 4-propyl-5,7-dihydroxycoumarin (Games and Haskins, *J. Chem. Soc. Chem. Commun.*, 1971, 1005).

The preparation of 5,7-dihydroxycoumarin monosulphonate esters by direct sulphonylation of 5,7-dihydroxycoumarin has been reported by Desai and Parghi,*J Indian Chem. Soc.*, 1956, 33, 661. The yield obtained for the preparation of 4-methyl-8-hydroxy-7-coumarinyl-4-toluenesulphonate by this procedure was 36%.

SUMMARY OF THE INVENTION

This invention is based on the discovery of an efficient process that, starting from a 5,7-dihydroxycoumarin, provides a 5-hydroxy-2H-pyrano[2,3-f]chromen-8-one according to the overall transformation depicted below, thus providing the ABC portion of the calanolide ring system.

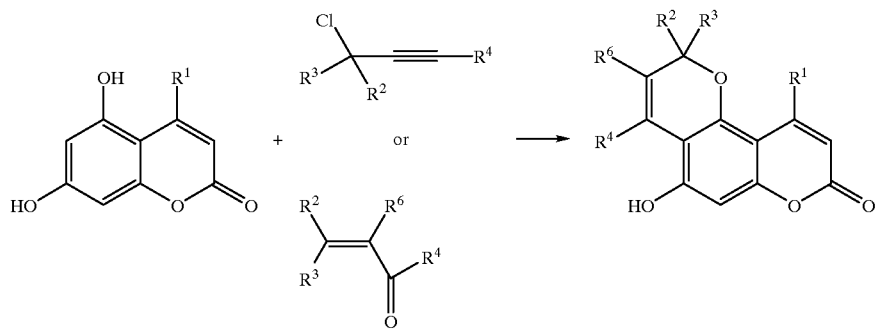

In these formulae, $R^1$, $R^2$, $R^3$, $R^4$ and $R^6$ each represent H or an organic group of up to 20 C atoms, or any pair of $R^2$ and $R^3$ or $R^2$ and $R^6$ or $R^4$ and $R^6$ forms a cyclic group, and $R^5SO_2$ is a cleavable protecting group in which $R^5$ is an organic group of up to 20 C atoms.

More particularly, the present invention provides a novel four-step procedure for accomplishing this regioselective chromene annulation, in which the key step is the unexpected 5-selective desulphonylation of a 5,7-disulphonyl ester of a 5,7-dihydroxycoumarin, to give a 5-hydroxy-7-coumarinyl sulphonate. Chromene annulation with, e.g. a propargyl halide or α,β-unsaturated aldehyde or ketone, provides the 5-hydroxy-2H-pyrano[2,3-f]chromen-8-one ring system. In particular, reaction of the compound wherein $R^1$=propyl with a $C_5$ synthon, e.g. 3-chloro-3-methylbut-1-yne, followed by cleavage of the remaining 7-sulphonyl group, provides 5-hydroxy-2,2-dimethyl-10-propyl-2H-pyrano[2,3-f]chromen-8-one. Palladium-catalysed asymmetric allylic substitution of this tricyclic phenol with tiglyl methyl carbonate, analogous to the process disclosed by Trost and Toste, provides both (R)- and (S)-5-(1,2-dimethyl-2-propenyloxy)-2,2-dimethyl-10-propyl-2H-pyrano[2,3-f]chromen-8-one in enantiomerically enriched form, thereby giving overall a particularly effective synthesis of calanolide A, e.g. by means of the steps disclosed by Trost and Toste and summarised above.

DESCRIPTION OF THE INVENTION

The preparation of 2H-pyrano[2,3-f]chromen-8-ones from 5,7-dihydroxycoumarins and the use of the invention for the formal synthesis of (+) and (−)-calanolides A and B are shown in Scheme I. Typically, $R^1$, $R^2$, $R^3$, $R^4$ and $R^6$ are each H, or alkyl or aryl, e.g. of up to 10 carbon atoms. Any ring that they form may be within the given definitions, including any (optional) substituents. Preferably, $R^1$ is propyl, $R^2$ and $R^3$ are each methyl, and $R^4$ and $R^6$ are each H.

Step (i) of the Scheme is the disulphonylation reaction. This is achieved using a sulphonyl chloride $R^5SO_2Cl$ in which $R^5$ may be an aryl group such as 4-tolyl or an alkyl group such as methyl.

Step (ii) is the 5-selective desulphonylation. This is preferably achieved using a fluoride reagent which may be a quaternary ammonium salt such as tetra-n-butylammonium fluoride or a metal salt such as potassium fluoride.

Step (iii) is the chromene annulation reaction. This is preferably achieved using, e.g. a propargyl halide or α,β-unsaturated aldehyde or ketone.

Step (iv) is the cleavage of the 7-sulphonyl group. This is preferably achieved using a fluoride reagent which may be tetra-n-butylammonium fluoride (TBAF).

Step (v) is the asymmetric allylic substitution reaction. This is achieved using a tiglyl electrophile which may be (E)-2-methyl-2-butenyl methyl carbonate, a base which may be caesium carbonate and a catalyst prepared from a phosphine ligand which may be (+)-1,2-bis-N-[2'-diphenylphosphino)benzoyl]-1(R),2(R)-diaminocyclohexane or (+)-1,2-bis-N-[2'-diphenylphosphino)benzoyl]-11(R), 12(R)-diamino-9,9,10-dihydro-9, 10-ethanoanthracene for the synthesis of (+)-calanolides A or B, or the opposite enantiomeric ligands for the synthesis of (−)-calanolides A or B, and a palladium reagent which may be tris(dibenzylideneacetone)dipalladium(0)-chloroform adduct.

The remaining steps shown by the Scheme are representative of the conversions required to complete the synthesis of calanolide compounds, as disclosed by Trost and Toste and summarised above.

Thus, the present invention provides a practical route by means of certain novel intermediates, to the ABC ring synthon for the calanolides and analogous antiviral xanthones. In particular, the 5-selective desulphonylation provides an efficient means for preparation of a robust 7-protected 5,7-dihydroxycoumarin. Protection of the 7-phenol ensures direction of the chromene annulation to the free 5-phenol, resulting in a selective overall process.

The following Examples illustrate the invention and its application to the synthesis of both (+) and (−)-calanolide A.

EXAMPLE 1

4-Propyl-5,7-coumarinyl ditosylate

Pyridine (260 ml) was added to 4-propyl-5,7-dihydroxycoumarin (100 g, 0.45 mol). Initially, the temperature rose to about 42° C. The suspension was stirred for 20 minutes, then tosyl chloride (190 g, 1.00 mmol) was added over 30 minutes while cooling with an ice/water bath, maintaining the internal temperature between 5 and 20° C. The suspension was stirred for 4 h, during which the temperature was allowed to rise from 10 to 23° C. Extra tosyl chloride (17 g) was added and the suspension was stirred for a further 30 minutes. The reaction was quenched by addition of water (100 ml) over 15 minutes. Toluene (600 ml) was added, followed by 2N HCl (1 L) over 10 minutes. The layers were allowed to separate and the organic layer was washed with 2N HCl (250 ml), saturated sodium carbonate solution (250 ml) and brine (250 ml), and dried ($MgSO_4$) and filtered. The solvent was evaporated, to give the crude ditosylate as a brown solid (243.6 g, 101.5% Th.). A small quantity of crude ditosylate (967 mg) was purified by recrystallisation from methanol, to give pure ditosylate as a white, granular solid (837 mg, 87% Th); mp 112° C.; ir $v_{max}$(KBr) 1743, 1611, 1371, 1422, 1193, 1227, 1183, 1139, 1067, 1006, 878, 814, 761, 720, 686, 668 and 555 cm$^{-1}$; $^1$H nmr (400 MHz, CDCl$_3$) δ ppm 7.78 (2H, d, J 8.3 Hz), 7.73 (2H, J 8.3), 7.40 (2H, J 8.2 Hz), 7.37 (2H, 8.2 Hz), 6.87 (1H, d, J 2.3 Hz), 6.75 (1H, d, J 2.3 Hz), 6.20 (1H s), 2.84 (2H, t, J 7.7 Hz), 2.50 (3H, s), 2.48 (3H, s), 1.59–1.53 (2H, m) and 0.94 (3H, t, H 7.3 Hz).

EXAMPLE 2

4-Propyl-5-hydroxy-7-coumarinyl-7-toluenesulphonate

THF (220 ml) was added to crude ditosylate (Example 1, 116.3 g, 220 mmol). The reaction flask was purged with nitrogen, and the suspension was stirred until most of the ditosylate had dissolved. The suspension was cooled to 0° C., and tetra-n-butylammonium fluoride (1M in THF, 220 ml) was added over 30 minutes, keeping the temperature in the range −5 to +2° C. During the addition, the ditosylate dissolved, to give a dark solution. The solution was stirred at −5 to +2° C. for 15 minutes, then ethyl acetate (440 ml), saturated ammonium chloride solution (330 ml) and water (110 ml) were added. The aqueous layer was removed and the organic phase was washed with 0.75M KHSO$_4$ (800 ml) and 2M KHSO$_4$ (4×250 ml). During these acid washes, a precipitate of monotosylate formed in the organic phase. The organic layer was washed with brine-saturated sodium bicarbonate solution (400 ml+100 ml), diluted with acetone (800 ml), dried (MgSO$_4$) and filtered. The MgSO$_4$ was swirled with THF (300 ml), and the suspension was filtered. The combined filtrates were evaporated to dryness. Isopropyl acetate (550 ml) was added, and the suspension was heated to reflux, then allowed to stir over 15 h while cooling to room temperature. The suspension was filtered and the solid was washed with isopropyl acetate (150 ml) and dried, to give the 7-monotosylate as a fine white solid (65.6 g, 79.6%); mp 210° C.; ir $v_{max}$ (KBr)3150 (br), 3092, 2967, 1674, 1610, 1429, 1380, 1344, 1289, 1238, 1193, 1180, 1126, 1093, 1047, 1014, 851, 813, 790, 718, 676, 593, 546 and 531 cm$^{-1}$; $^1$H mnr (400 MHz, acetone d-6) δ ppm 10.3 (1H, brs), 7.82 (2H, d, J 8.4 Hz), 7.53 (2H, J 8.2 Hz), 6.62 (1H, d, J 2.4 Hz), 6.47 (1H, d, J 2.4 Hz), 6.08 (1H s), 2.97 (2H, t, J 7.7 Hz), 2.48 (1H, s), 1.67 (sextet, J 7.4 Hz) and 1.00 (3H, t, J 7.3 Hz)

EXAMPLE 3

5-(4-Toluenesulphonyloxy)-2,2-dimethyl-10-propyl-2H-pyrano[2,3-f]chromen-8-one

The 7-tosylate (Example 2, 3.50 g, 9.35 mmol) and potassium carbonate (3.23 g, 23.4 mmol) were placed in a flask. 2-Butanone (50 ml) and DMF (5 ml) were added. The reaction flask was purged with nitrogen and 3-chloro-3-methyl-1-butyne (3.15 ml, 28 mmol) was added. Zinc chloride (1.66 g 12.1 mmol) was added and the suspension was heated to reflux for 5 h. Extra 3-chloro-3-methyl-1-butyne (1.4 ml, 12.5 mmol) was added, and the suspension was heated to reflux for 2 h, and then allowed to cool to room temperature overnight. The mixture was diluted with toluene (50 ml), and then saturated ammonium chloride solution (50 ml) and water (10 ml) were added. The aqueous layer was removed and the organic layer was washed with saturated KHSO$_4$-water (50 ml+10 ml), saturated NaHCO$_3$-water (50 ml+10 ml), dried (MgSO$_4$), and filtered. After evaporation of the solvent, methanol (50 ml) was added, and the suspension was heated to reflux, allowed to cool to room temperature, stirred for 30 minutes at room temperature, then filtered, to give the tricyclic chromene as a white granular solid after drying (1.73 g, 42%). After concentration of the mother liquors to ca. 10 ml, a second crop of tricyclic chromene of lower purity was obtained (303 mg 7%); mp 148° C.; ir $v_{max}$(KBr) 1731, 1616, 1592, 1570, 1420, 1400, 1382, 1216, 1194, 1181, 1141, 1119, 1094, 1059, 1046, 1024, 885, 842, 788, 731, 670 and 559 cm$^{-1}$; $^1$H nmr (400 MHz, CDCl$_3$) δ ppm 7.77 (2H, d, J 8.2 Hz), 7.35 (2H, d, J 8.2 Hz), 6.47 (1H, d, J 10.0 Hz), 6.44 (1H, s),6.08 (1H, s), 5.57 (1H, d, J 10.0 Hz), 2.88 (2H, t, J 7.7 Hz), 1.69–1.59 (2H, m), 1.45 (6H, s) and 1.03 (3H, t, J 7.3 Hz).

EXAMPLE 4

5-Hydroxy-2,2-dimethyl-10-propyl-2H-pyrano[2,3-f]chromen-8one

The tricyclic chromene (Example 3, 14.3 g, 32.5%) was suspended in THF (30 ml). Tetra-n-butylammonium fluoride (1M in THF, 39.5 ml) was added over 5 minutes. The suspension was stirred for 10 minutes, and then ethyl acetate (50 ml) and saturated ammonium chloride solution were added. The mixture was stirred vigorously, the layers were allowed to separate, and the aqueous layer was removed. The organic layer was washed with saturated KHSO$_4$-water (50 ml+10 ml), saturated KHSO$_4$-water (10 ml+10 ml) and brine-saturated NaHCO$_3$ (40 ml+10 ml), dried (MgSO$_4$), and filtered. After evaporation of the solvent, isopropyl acetate (40 ml) was added, the mixture was heated to refux, then stirred for 2 h while allowing to cool to room temperature, then filtered to give the tricyclic monophenol as an pale yellow granular solid (5.1 g, 55%). A second crop of lower purity (632 mg) was also obtained; mp 190° C.; m/z (GCMS, EI) 286 (18%), and 271 (100); $v_{max}$ (KBr) 3150 (br), 2964, 1686, 1643, 1579, 1453, 1423, 1382, 1354, 1290, 1254, 1216, 1158, 1120, 1102, 1091, 1047, 840, 834 and 692 cm$^{-1}$; $^1$H NMR (400 MHz, acetone d-6) δ ppm 9.7 (1H, brs), 6.69 (1H, d, J 9.91 Hz), 6.38 (1H s), 5.90 (1H, s), 5.68 (1H, d, J 10.0 Hz), 2.93 (2H, t, J 7.8 Hz), 1.70 (2H, sextet, J 7.5 Hz), 1.53 (6H, s) and 1.06 (3H, t, J 7.3 Hz).

EXAMPLE 5

4-Propyl-5,7-coumarinyl-dimesylate

Methanesulfonyl chloride was added to a stirred suspension of 4-propyl-5,7-coumarindiol (10.0 g, 45.5 mmol) and potassium carbonate (15.70 g, 113.8 mmol) in THF (210 ml) under nitrogen. After 21 hours, the reaction mixture was diluted with ethyl acetate (200 ml) and was poured into saturated sodium carbonate (80 ml) in an ice-water bath. After stiring for 10 minutes, the phases were separated and the organic phase sequentially washed with saturated sodium carbonate (2×100 ml), and brine (100 ml) and then dried (Na$_2$SO$_4$). Filtration followed by concentration in vacuo provided the crude dimesylate as a white solid (15.7 g, 92%). $^1$H NMR (200 MHz, CDCl$_3$) δ ppm 7.33 (1H, d, J 2.5), 7.26 (1H, d, J 2.5), 6.32 (1H, s), 3.33 (3H, s), 3.26 (3H, s), 2.95 (2H, t, J 7.2), 1.74–1.61 (2H, m) and 1.06 (3H, t, J 7.2).

EXAMPLE 6

4-Propyl-5-hydroxy-7-coumarinyl-7-mesylate

TBAF (2.66 ml of a 1M solution in THF, 2.66 mmol) was added dropwise to an ice-water bath cooled, stirred suspension of 4-propyl-5,7-coumarinyl-dimesylate (Example 5, 1.00 g, 2.66 mmol) in THF (2.66 ml) under a nitrogen atmosphere. After stirring for one hour, the mixture was diluted with ethyl acetate (20 ml) and sequentially washed with 1M potassium hydrogensulfate solution (5×20 ml), brine (20 ml ) and then dried (Na$_2$SO$_4$). Filtration followed by concentration in vacuo provided the crude product as a 10:1 regioisomeric mixture, as determined by $^1$H NMR spectroscopy. The crude product was recrystallised from isopropyl acetate (5 ml) to provide the title product as a white solid (482 mg, 61%).

Alternatively, potassium fluoride (58 mg, 1.0 mmol) and tris[2-(2-methoxyethoxy)ethyl]amine (320 μl, 1.0 mmol) were added to a solution of 4-propyl-5,7-coumarinyl-dimesylate (Example 5, 376 mg, 1.00 mmol) in DME (1 ml) and water (1 ml) which had been purged with nitrogen. The solution was heated to reflux with stiring for 24 hours. After cooling to room temperature, the mixture was diluted with ethyl acetate (10 ml) and sequentially washed with saturated potassium hydrogen sulfate solution (5×5 ml) and brine (10 ml), and then dried (Na$_2$SO$_4$). Filtration followed by concentration in vacuo provided the title compound as a 5.6:1 mixture of regioisomers in 93% conversion, as determined by $^1$H NMR spectroscopy. $^1$H NMR (200 MHz, CD$_3$OD) δ ppm 6.70 (1H, d, J 2.4), 6.60 (1H, d, J 2.4), 5.99 (1H, s), 3.18 (3H, s), 2.88 (2H, t, J 8.1), 1.67–1.48 (2H, m) and 0.92 (3H, t, J 7.3); signals for the regioisomer are discernible at 6.84 (1H, d, J 2.0) and 3.27 (3H, s).

EXAMPLE 7

2,2-Dimethyl-5-methanesulfonyloxy-10-propyl-2H-pyrano[2,3-f]chromen-8-one

The monophenol (Example 6, 2.50 g, 8.39 mmol), potassium carbonate (2.90 g, 21.0 mmol), methyl ethyl ketone (42 ml) and DMF (4.2 ml) were placed in a flask and nitrogen was bubbled through the stirred solution for 5 minutes. 3-Chloro-3-methylbut-1-yne (4.25 ml, 37.8 mmol), tetrabutylammonium iodide (3.10 g, 8.39 mmol) and zinc(II) chloride (1.48 g, 10.90 mmol) were then sequentially added and the whole mixture was heated at reflux. After four hours, the mixture was cooled to room temperature and diluted with ethyl acetate (100 ml) and then sequentially washed with saturated ammonium chloride (50 ml), saturated potassium hydrogen sulfate (50 ml), saturated sodium bicarbonate (50 ml) and brine (50 ml). The organic phase was then dried ($Na_2SO_4$), filtered and concentrated in vacuo. The crude material was treated to a hot slurry with methanol (40 ml) to provide the title compound, following filtration, as a white fluffy solid (1.40 g, 45%). $^1$H NMR (200 MHz, $CDCl_3$) δ ppm 6.87 (1H, s), 6.60 (1H, d, J 10.0), 6.11 (1H, s), 5.71 (1H, d, J 10.0), 3.24 (3H, s), 2.90 (2H, t, J 7.2), 1.73–1.61 (2H, m), 1.53 (6H, s) and 1.05 (3H, t, J 7.3).

EXAMPLE 8

5-Hydroxy-2,2-dimethyl-10-propyl-2H-pyrano[2,3-f]chromen8-one

TBAF (1.92 ml of a 1M solution in THF, 1.92 mmol) was added dropwise to an ice-water bath cooled stirred suspension of the mesylate Example 7, 700 mg, 1.92 mmol) in THF (2 ml) under nitrogen. After stirring for two hours, the mixture was diluted with ethyl acetate (10 ml) and sequentially washed with saturated potassium hydrogen sulfate (5×10 ml), water (10 ml) and brine (10 ml). The organic phase was then dried ($Na_2SO_4$), filtered and concentrated in vacuo. The crude product was purified by carrying out a hot slurry with isopropyl acetate (4 ml) to provide the title product as a white solid (340 mg, 62%). This was identical to material prepared by an alternative route.

EXAMPLE 9

(R)-(3-Methyl-3-buten-2-yl)oxy-2,2-dimethyl-10-propyl-2H-pyrano[2,3-f]chromen-8-one 5-Hydroxy-2,2dimethyl-10-propyl-2H-pyrano[2,3-f]chromen-8-one (Example 8, 2.03 g, 7.08 mmol) was suspended in dichloromethane (20 ml). Nitrogen was bubbled through the suspension for 15 minutes, then caesium carbonate (115 mg, 0.35 mmol) was added, followed by (+)-1,2-bis-N-[2'-(diphenylphosphino)benzoyl]-1(R),2(R)-diaminocyclohexane (285 mg, 0.42 mmol) and dipalladium tris(dibenzylidineacetone)-chloroform adduct (183 mg, 0.35 mmol). The suspension was stirred under nitrogen for 15 minutes, and then (E)-2-methyl-2-butenyl methyl carbonate (3.06 g, 21.2 mmol) was added. The red/brown suspension was heated to reflux under nitrogen for 3.5 h, then the yellow solution was cooled to room temperature. Silica gel (10 g) was added and the solvent was evaporated. The dried silica was applied to a silica column packed in heptane-ethyl acetate (6:1). Elution with heptane-ethyl acetate (6:1) provided the (R)-allylic ether in a 3.3:1 mixture with its allylic regioisomer, i.e. (E)-2-methyl-2-butenyl)oxy-2,2-dimethyl-10-propyl-2H-pyrano[2,3-f]chromen-8-one, as a yellow oil (2.61 g, 104 wt %); ir $v_{max}$ (NaCl, film) 2974, 1732, 1641, 1593, 1560, 1465, 1593, 1420, 1367, 1342, 1253, 1159, 1121, 1106 and 1051 $cm^{-1}$; $^1$H nmr (400 MHz, $CDCl_3$) δ ppm 6.69 (1H, d, J 9.9 Hz), 6.37 (1H, s), 5.94 (1H, s), 5.53 (1H, d, J 9.9 Hz), 5.01 (1H, s), 4.93 (1H, s), 4.76 (1H, q, J 6.42 Hz), 2.94–2.83 (2H, m), 1.72 (3H, s), 1.69–1.56 (2H, m), 1.49 (6H, s) and 1.03 (3H, J 7.4 Hz); $^{13}$C nmr (100 MHz, $CDCl_3$) δ ppm 161.7, 158.5, 156.5, 152.0, 144.9, 127.2, 117.1, 113.3, 111.2, 107.9, 104.3, 95.1, 78.5, 78.0, 74.9, 38.8, 28.2, 28.1, 23.6, 20.8, 17.7 and 14.5; enantiomeric excess 88% by chiral HPLC.

EXAMPLE 10

(S)-(3-Methyl-3-buten-2-yl)oxy-2,2-dimethyl-10-propyl-2H-pyrano[2,3f]chromen-8-one 5-Hydroxy-2,2-dimethyl-10-propyl-2H-pyrano[2,3-f]chromen-8-one (Example 8, 107 mg, 0.37 mmol) and caesium carbonate (6 mg, 0.019 mmol) were placed in a flask. A solution of (E)-2-methyl-2-butenyl methyl carbonate (108 mg, 0.75 mmol) in dichloromethane (1 ml) was added. Meanwhile, a solution of (−)-1,2-bis-N-[2'-(diphenylphosphino)benzoyl]-11(S),12(S)-diamino-9,10-dihydro-9,10-ethanoanthracene and then dipalladium tris (dibenzylidineacetone)-chloroform adduct (9.5 mg, 0.025 mmol) in dichloromethane (0.5 mmol) was prepared, then added to the reaction. The suspension was heated to reflux for 8 h, then the yellow solution was allowed to cool to room temperature. After adsorption onto silica (500 mg), and elution with heptane-ethyl acetate (9:1), the (S)-allylic ether in a 11:1 mixture with its allylic regioisomer, i.e. (E2-methyl-2-butenyl)oxy-2,2-dimethyl-10-propyl-2H-pyrano[2,3-f]chromen-8-one, was obtained as a yellow oil (132 mg, 100%); enantiomeric excess 94% by chiral HPLC.

Scheme 1

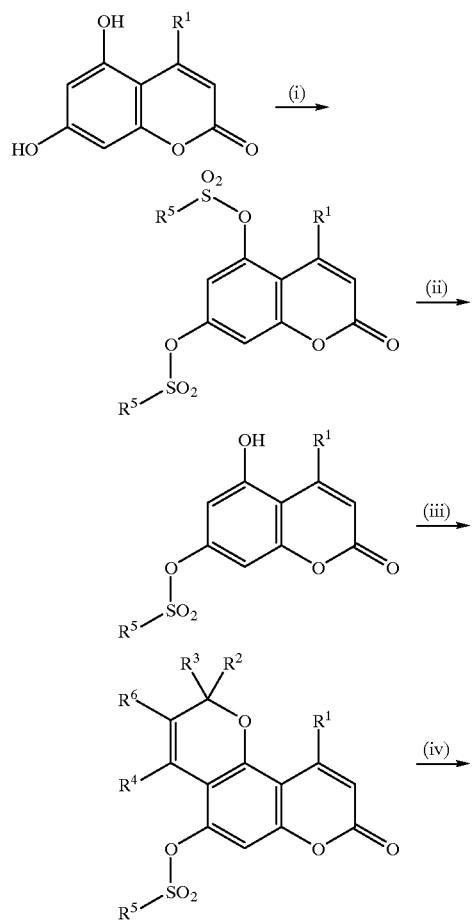

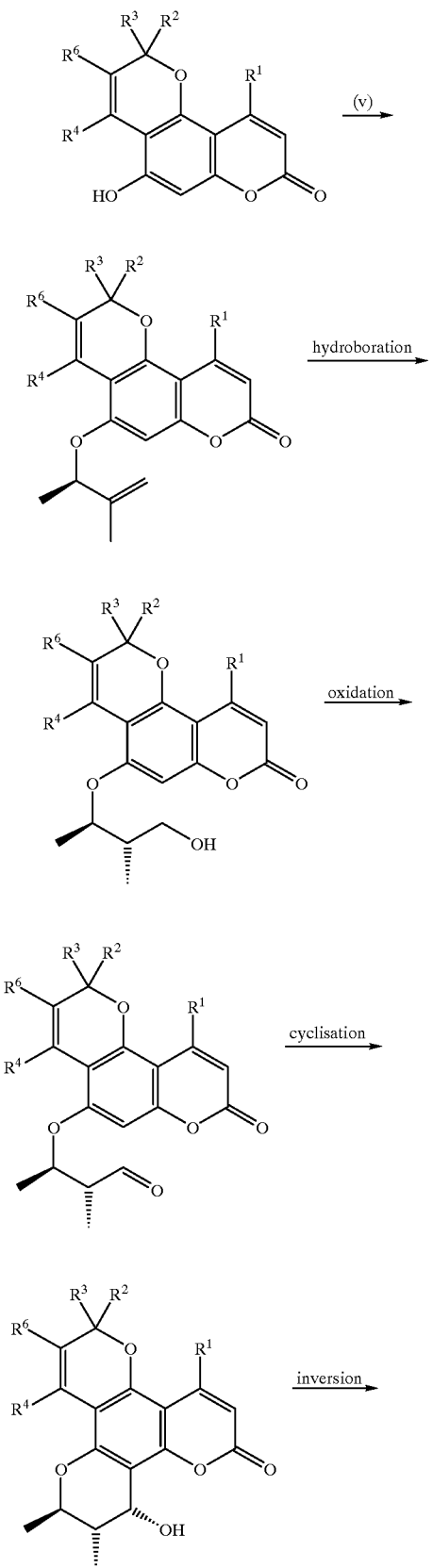

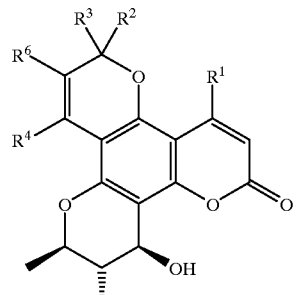

What we claim is:

1. A compound formula

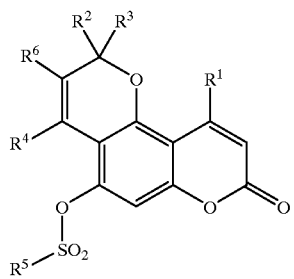

wherein $R^1$, $R^2$, and $R^3$ are each, independently, an alkyl or aryl group of up to 10 C atoms; $R^4$ and $R^6$ are each hydrogen; and $R^5SO_2$ is a cleavable protecting group in which $R^5$ is an organic group of up to 20 C atoms.

2. The compound according to claim 1, wherein $R^1$ is propyl and $R^2$ and $R^3$ are each methyl.

3. The compound according to claim 1, wherein $R^5$ is an aryl or allyl group of up to 10 C atoms.

4. The compound according to claim 3, wherein $R^5$ is 4-tolyl.

5. The compound according to claim 3, wherein $R^5$ is methyl.

6. A process for preparing the corresponding 5-hydroxy-2H-pyrano[2,3-f]chromen-8-one from a compound of claim 1, by cleavage of the O-sulphonyl group.

7. The process according to claim 6, for the preparation of 5-hydroxy-2,2-dimethyl-10-propyl-2H-pyrano[2,3-f]chromen-8-one.

8. A process for preparing a compound according to claim 1, which comprises reacting from a 5-hydroxy-7-sulphonyloxycoumarin with a reagent providing a unit of 3 carbon atoms for formation of the chromene ring.

9. The process according to claim 8, wherein the reagent is of formula

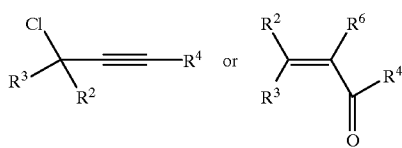

wherein the R groups are as defined in claim 1.

10. The process according to claim 9, which comprises reaction of a 4-propyl-5-hydroxy-7-coumarinyl-sulphonate with 3-chloro-3-methylbut-1-yne.

11. The process according to claim 8, which comprises the prior steps of di-O-sulphonylation of a 5,7-dihydroxycoumarin followed by selective cleavage of the 5-sulphonyl group.

12. The process according to claim 11, wheren a fluoride reagent is used for cleavage of the sulphonyl group.

13. The process according to claim 12, wherein the fluoride reagent is tetra-n-butylammonium fluoride.

14. The process according to claim 12, wherein the fluoride reagent is potassium fluoride.

15. A process for preparing an antiviral compound of the canalolide class, which comprises the process of claim 6 and conversion of the 5-hydroxy-2H-pyrano[2,3-f]chromen-8-one intermediate by palladium-catalysed asymmetric allylic substitution with a tiglyl methyl carbonate analogue, and converting the product to the antiviral compound.

16. The process according to claim 15, wherein the 5-hydroxy-2H-pyrano[2,3-f]chromen-8-one intermediate is 5-hydroxy-2,2-dimethyl-10-propyl-2H-pyrano[2,3-f]chromen-8-one.

17. The process according to claim 15, wherein the palladium catalyst is a complex of a ligand selected from the group consisting of (+)-1,2-bis-N-[2'-(diphenylphosphino)-benzoyl]-1(R),2(R)-diaminocyclohexane, (+)-1,2-bis-N-[2'-(diphenylphosphino)-1'-napthoyl]-1(R),2(R)-diaminocyclohexane, and (−)-1,2-bis-N-[2'-diphenylphosphino)benzoyl]-11(R),12(R)diamino-9,10-dihydro-9,10-ethanoanthracene, and the opposite enantiomers thereof.

18. The process according to claim 15, wherein the tiglyl methyl carbonate analogue is selected from the group consisting of (E)-2-methyl-2-butenyl methyl carbonate, 1,2-dimethyl-2-propenyl methyl carbonate and (E)-1,1-diacetoxy-2-methyl-2-butene.

* * * * *

UNITED STATES PATENT AND TRADEMARK OFFICE
CERTIFICATE OF CORRECTION

PATENT NO.   : 6,313,320 B1
DATED        : November 6, 2001
INVENTOR(S)  : Martin Edward Fox and Graham Andrew Meek Page 1 of 1

It is certified that error appears in the above-identified patent and that said Letters Patent is hereby corrected as shown below:

<u>Column 10,</u>
Line 46, "allyl" should read -- alkyl --.

<u>Column 11,</u>
Line 17, "wheren" should read -- wherein --.
Line 24, "canalolide" should read -- calanolide --.

Signed and Sealed this

Twenty-first Day of May, 2002

JAMES E. ROGAN
Director of the United States Patent and Trademark Office

Attest:

Attesting Officer